(12) United States Patent
Kerr

(10) Patent No.: US 7,604,648 B2
(45) Date of Patent: Oct. 20, 2009

(54) DIRECT VISION PORT SITE DISSECTOR

(75) Inventor: Stephen Kerr, Sunset Beach, CA (US)

(73) Assignee: Intellimed Surgical Solutions, LLC, San Juan Capistrano, CA (US)

( * ) Notice: Subject to any disclaimer, the term of this patent is extended or adjusted under 35 U.S.C. 154(b) by 0 days.

(21) Appl. No.: 10/530,703

(22) PCT Filed: May 27, 2003

(86) PCT No.: PCT/US03/16575

§ 371 (c)(1), (2), (4) Date: Sep. 23, 2005

(87) PCT Pub. No.: WO2004/037097

PCT Pub. Date: May 6, 2004

(65) Prior Publication Data

US 2006/0079925 A1  Apr. 13, 2006

(51) Int. Cl.
*A61M 29/00* (2006.01)
(52) U.S. Cl. .......................................... 606/198; 606/15
(58) Field of Classification Search ................. 600/201, 600/204, 205, 210, 214, 216; 606/190, 108
See application file for complete search history.

(56) References Cited

U.S. PATENT DOCUMENTS

| | | | |
|---|---|---|---|
| 5,020,514 A | 6/1991 | Heckele | |
| 5,098,388 A | 3/1992 | Kulkaski et al. | |
| 5,104,394 A | 4/1992 | Knoepfler | |
| 5,178,133 A | * 1/1993 | Pena | ........................... 600/203 |
| 5,201,752 A | * 4/1993 | Brown et al. | ................. 606/190 |
| 5,256,149 A | 10/1993 | Banik et al. | |
| 5,282,807 A | 2/1994 | Knoepfler | |
| 5,354,302 A | * 10/1994 | Ko | ............................. 606/104 |
| 5,373,840 A | 12/1994 | Knighton | |
| 5,385,572 A | 1/1995 | Nobles et al. | |
| 5,431,151 A | 7/1995 | Riek et al. | |
| 5,441,041 A | 8/1995 | Sauer et al. | |
| 5,447,513 A | 9/1995 | Davison et al. | |
| 5,511,564 A | * 4/1996 | Wilk | ........................... 128/898 |
| 5,551,947 A | 9/1996 | Kaali | |

(Continued)

FOREIGN PATENT DOCUMENTS

DE    10037421 A    5/2002

(Continued)

*Primary Examiner*—Anhtuan T Nguyen
*Assistant Examiner*—Tuan V Nguyen
(74) *Attorney, Agent, or Firm*—Pepper Hamilton LLP

(57) ABSTRACT

A direct vision dissecting port for providing safe entry into a body cavity, as well as being operative to serve as a standard port for use in laparoscopic, endoscopic or thoracic surgery. The device includes an elongated housing within which a endoscope may be positioned. The distal-most end of the device allows for viewing of tissue dissection or gripping by tissue spreaders and is operatively transitional between a closed configuration and an open, operative configuration. Transition of the tissue spreaders between the two configurations selectively cuts tissue by a spreading action in a layer-by-layer fashion while under the direct vision of the endoscope disposed therein. The port may further optionally assume an anchor configuration once positioned within the patient to enable the same to remain securely in position during the surgical procedure.

13 Claims, 7 Drawing Sheets

U.S. PATENT DOCUMENTS

| | | | |
|---|---|---|---|
| 5,569,291 A * | 10/1996 | Privitera et al. | 606/185 |
| 5,569,292 A | 10/1996 | Scwemberger et al. | |
| 5,591,192 A | 1/1997 | Privitera et al. | |
| 5,609,562 A | 3/1997 | Kaali | |
| 5,632,717 A | 5/1997 | Yoon | |
| 5,653,726 A | 8/1997 | Kieturakis | |
| 5,667,478 A | 9/1997 | McFarlin et al. | |
| 5,676,682 A | 10/1997 | Yoon | |
| 5,683,349 A * | 11/1997 | Makower et al. | 600/214 |
| 5,720,761 A | 2/1998 | Kaali | |
| 5,738,628 A | 4/1998 | Sierocuk et al. | |
| 5,762,070 A * | 6/1998 | Nagamatsu | 600/564 |
| 5,797,906 A | 8/1998 | Makower et al. | |
| 5,843,017 A * | 12/1998 | Yoon | 604/22 |
| 5,860,996 A | 1/1999 | Urban et al. | |
| 5,984,919 A | 11/1999 | Hilal et al. | |
| 6,001,120 A | 12/1999 | Levin | |
| 6,120,437 A * | 9/2000 | Yoon et al. | 600/204 |
| 6,206,823 B1 | 3/2001 | Kolata et al. | |
| 6,228,097 B1 | 5/2001 | Levinson et al. | |
| 6,436,119 B1 * | 8/2002 | Erb et al. | 606/198 |
| 6,497,651 B1 * | 12/2002 | Kan et al. | 600/114 |
| 6,709,445 B2 * | 3/2004 | Boebel et al. | 606/207 |
| 6,770,026 B2 | 8/2004 | Kan et al. | |
| 7,056,329 B2 | 6/2006 | Kerr | |
| 2004/0093000 A1 | 5/2004 | Kerr | |

FOREIGN PATENT DOCUMENTS

| | | |
|---|---|---|
| EP | 1036544 A | 9/2000 |
| GB | 2125702 | 3/1984 |
| JP | 5-506176 | 9/1993 |
| JP | 9-500047 | 1/1997 |
| WO | WO 8303189 A | 9/1983 |
| WO | WO 2004/037097 A1 | 5/2004 |

* cited by examiner

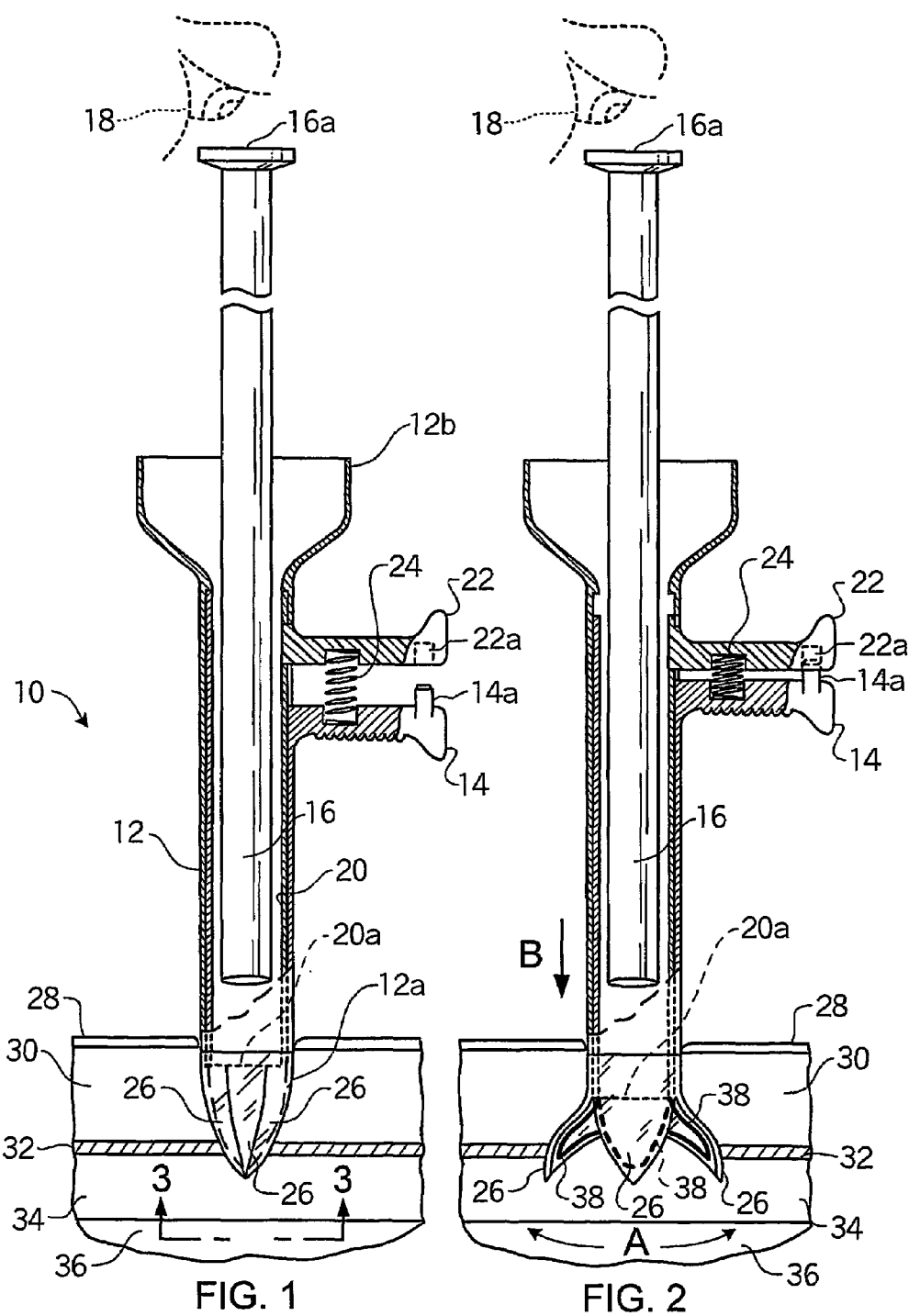

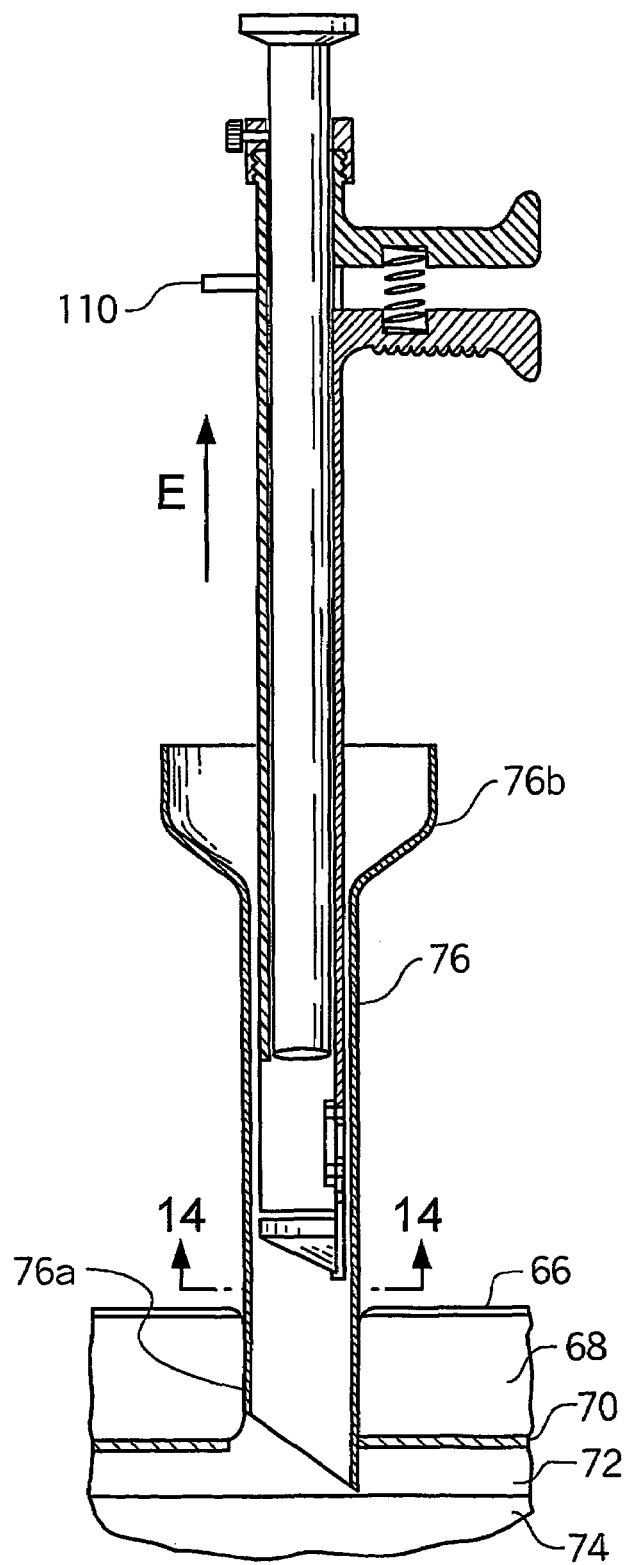
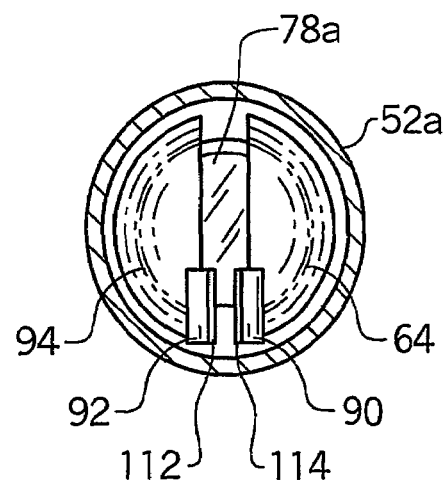
FIG. 14
FIG. 13

DIRECT VISION PORT SITE DISSECTOR

RELATED APPLICATIONS AND CLAIM OF PRIORITY

This application claims priority to, and incorporates by reference in their entirety, co-pending U.S. patent application Ser. Nos. 10/278,621, filed Oct. 23, 2002, titled "Direct Vision Port Site Dissector" and 10/278,572, filed Oct. 23, 2003 titled "Laparoscopic Direct Vision Dissecting Port".

BACKGROUND

Laparoscopic, thoracoscopic and other endoscopic procedures are well-known, widely utilized surgical techniques that advantageously reduce patient recovery time due to minimal tissue damage. Generally, these surgical techniques rely upon the formation of one or more puncture wounds through which a body cavity, such as the peritoneal or the thoracic cavity, can be accessed. In laparoscopic surgery, once the peritoneal cavity has been entered, the same is insufflated with carbon dioxide gas, typically to a pressure of approximately 15 mm Hg, followed by the introduction of an endoscopic port with inserted trocar, which may either be bladed or blunt. In thoracoscopic surgery, once the thoracic cavity has been entered, procedures can be performed either by the selective deflation of the lung on the side of the operation with subsequent placement of an endoscopic port, or by the creation of a controlled pneumothorax by insufflation of a limited amount of carbon dioxide gas through a port that is placed into the thoracic cavity which has an airtight seal.

In these procedures the port and cannula are essentially the same and function to accept by insertion a trocar for tissue penetration or an endoscope for viewing. Generally the terms laparoscope, thoracoscope, mediastinascope, arthoscope and other such viewing device will be referred to herein using the generic term 'endoscope'.

The endoscopic port with inserted trocar is placed into the peritoneal, thoracic or other body cavity, followed by the placement of a viewing device therethrough to thus provide visualization of the body cavity thus enabling the surgeon to view the surrounding organs and conduct the surgical procedure. Advantageously, the use of such ports placed through small diameter openings enables the patient to readily heal following surgery, and requires much less recuperation time for the patient as compared to open surgical procedures, which typically deploy long incisions which can and frequently are deemed traumatic to the patient and involve substantially longer recuperative periods. Despite its advantages, endoscopic surgery as currently performed can pose substantial risks to the patient. In this respect, it is widely recognized that entry into the body cavity during such surgery, due to the procedure by which the body cavity is accessed, can cause serious injury, for example, to the abdominal organs, such as the spleen, liver and intestine as well as blood vessels, or to the thoracic organs, such as the lung, heart, or blood vessels. In the abdomen, this risk is due in large part to the fact that in the unoperated abdomen, most surgeons enter the peritoneal cavity using a Veress needle which is pushed blindly through the patient's fascia and peritoneum. The peritoneal cavity is then insufflated followed by the introduction of the laparoscopic port with inserted blunt or bladed trocar, which also is pushed blindly into the peritoneal cavity. Once positioned therein, the trocar is removed and a laparoscope is introduced through the port to thus provide visualization within the cavity.

Problematic with such procedure, however, is the fact that the body cavity is entered blindly on two separate occasions: first, through the introduction of the Veress needle; and second, through the introduction of the laparoscopic port with inserted trocar, which can and on occasion does injure abdominal organs and blood vessels.

To the extent laparoscopic surgery is performed upon a patient that has previously undergone an abdominal operation, the preferred surgical practice is to enter the peritoneal cavity under direct vision. In this regard, it is known that when a patient has undergone previous abdominal surgery, the abdominal contents can become adherent to the abdominal wall, making blind placement of a Veress needle and then blind placement of the port with inserted trocar a much more risky technique.

Using a direct vision technique, the skin is incised and the subcutaneous tissue dissected until the fascia is encountered. The fascia is then dissected, typically by grasping the fascia with two surgical clamps and incising the fascia sharply followed by successively grasping the subfascial tissue until the peritoneum is encountered at which point the peritoneum is opened and the peritoneal cavity is entered under direct visualization. Once entered, the laparoscopic port is then placed in the peritoneal cavity under direct vision and the abdomen insufflated with carbon dioxide gas. This procedure, however, typically requires a larger skin incision than is typically produced via the use of the Veress needle technique, particularly with respect to obese patients, and is furthermore prone to gas leakage during surgery, thus requiring constant monitoring and maintenance of adequate insufflation.

In light of such potential complications that can arise via entry into the peritoneal cavity during laparoscopic surgery, attempts have been made to provide means for safely entering into a body cavity utilizing direct visualization. Exemplary of such devices are those disclosed in U.S. Pat. No. 5,441,041, issued to Sauer, et al., entitled Optical Trocar, issued Aug. 15, 1995, which utilizes a blade moveable between a non-deployed position and a deployed position to thus allow dissection under visualization of an endoscope. Such device, however, does not allow for any type of spreading of the cut tissue to enable the surgeon to see the next layer of tissue to be entered. As such, dissection is performed without prior visualization thereof.

A similar device attempting to provide direct visualization during entry into a body cavity is shown in U.S. Pat. No. 5,569,291, issued to Privitera, et al., entitled Surgical Penetration and Dissection Instrument, issued on Oct. 29, 1996. Such reference discloses a device for forming an entry into a body cavity performed under direct visualization of an endoscope. The dissecting portion of the device consists of a clear plastic conical tip with elevated dissecting blades that is advanced into the tissue via a twisting motion. The conical tip, however, is advanced bluntly into the tissue before the same can be identified and, as a consequence, incision of the tissue is performed without prior visualization. In fact, inadvertent entry into an organ cannot be avoided via use of such device, and it is only after the organ is entered, and hence damaged, that such matter can be appraised. Moreover, the use of clear plastic has substandard optical visualization due to optical properties inherent in such material, coupled with the conical shape, such that advancement of the tip fails to provide a clear visualization as the same is advanced through tissue.

Other devices that are similar in nature include U.S. Pat. No. 5,720,761, issued to Kalli on Feb. 24, 1998 entitled Visually Directed Trocar and Method; U.S. Pat. No. 5,551, 947, issued to Kalli on Sep. 3, 1996, entitled Visually Directed Trocar for Laparoscopic Surgical Procedures and Methods of Using the Same; U.S. Pat. No. 5,609,562, issued to Kalli on Mar. 11, 1997 entitled Visually Directed Trocar and Method; and U.S. Pat. No. 5,385,572, issued to Nobles, et al. on Jan. 31, 1995 entitled Trocar for Endoscopic Surgery, the teachings of all of which are expressly incorporated herein by reference.

A further related surgical instrument is disclosed in U.S. Pat. No. 5,354,302, issued to Ko entitled Medical Device and Method for Facilitating Intra-Tissue Visual Observation and Manipulation of Distensible Tissues. Essentially, such device comprises an elongated sheath having a cone-shaped distal end and inner sheath member disposed therein within operative to cause the distal end to move tissue away to thus enable tissue to be manipulated and visualized by the inner sheath member. While the cone-shaped distal end is operative to move tissue away such that visualization of tissues and the like can be enhanced, such cone-shaped distal end does not provide any dissection function. Indeed, the flaps of the distal end of the cone member are flimsy in nature and non-reinforced. As such, the same are ill suited for enhancing direct visualization, much less providing any type of dissecting function. Such device is further not designed for use in laparoscopic applications, and in particular a laparoscopic port through which other instruments can be positioned and deployed.

There is thus a substantial need in the art for a system and method that can enable a surgeon to selectively enter a body cavity, vessel, or organ, for purposes of performing endoscopic procedures whereby the surgeon is provided with direct visualization during entry such that tissue separation can be visualized and organ and tissue damage can be avoided (i.e., the surgeon can see the tissue prior to dissecting the same). There is additionally a need for such a device and system that is capable of forming an entry into a body cavity via a skin incision no greater than that required to admit the introduction of an endoscopic port and that also preferably forms a tight seal around the port following its introduction such that gas leakage during the surgical procedure is minimized. Still further, there is need for such a system and method which provide for cavity entry without prior insufflation of gas into the cavity but can preferably have a means to insufflate the body cavity following entry, if desired.

SUMMARY

The present invention specifically addresses and alleviates the above-identified deficiencies. In this regard, the present invention is directed to a direct vision port site dissector operative to selectively and sequentially dissect or cut through tissue by a spreading action. Dissection by spreading of tissue under direct vision of a viewing device minimizes damage to tissue, vasculature and organs in a patient. The direct vision port site dissector may be used to selectively dissect or biopsy tissue or it may be used to position a port into a body cavity which may thereafter be utilized in a variety of surgical procedures and equipment placements.

In the practice of embodiments of the present invention the terms port and cannula are essentially the same and each functions to accept by insertion a trocar for tissue penetration or an endoscope for viewing. Generally the terms laparoscope, thoracoscope, mediastinascope, arthroscope and other such viewing device will be referred to herein using the generic term 'endoscope'.

In the embodiments of the present invention the trocars may range in size from about 2.5 mm to about 24 mm, and preferably from about 5 mm to about 12 mm. As those skilled in the art will appreciate, the present invention may be manufactured from a number of different of materials including, without limitation, biologically compatible metals, alloys, ceramics, plastics, or elastomers.

According to one embodiment of the present invention, the tissue dissector device consists of an elongated housing having a proximal end and a distal end, the latter being operative to be inserted through a skin incision made upon the patient. Disposed at the distal end of the housing is a tissue spreader dissecting mechanism which includes one or more tissue spreaders which are operative to extend from the distal-most opening of the housing and selectively spread apart, or grip the various layers of tissue encountered as the distal-most end of the device is advanced through the successive tissue layers and into a body cavity, organ, or vessel. Disposed within the housing is a viewing device for viewing the dissection or biopsy of tissue by the tissue spreaders as the device penetrates through or alternatively, grasps the tissue.

The tissue spreaders are operatively coupled to the distal end of an actuator which may be a rod or cylinder which is itself operatively coupled at its proximal end to an actuator mechanism. The actuator mechanism transmits a force through the actuator bar, rod, or cylinder which is coupled to the tissue spreader through a tissue spreading dissecting mechanism. The handle or other actuator mechanism transmits a force through the actuator extending from the proximal end of the housing and causes the tissue spreading dissecting mechanism, and hence the tissue spreaders, to be selectively controlled as may be necessary for any anatomical considerations that are visually perceived by the physician. With respect to a handle actuator mechanism, the same is preferably connected to an actuator coupled to the handle member, the actuator being operatively coupled to the tissue spreading dissector mechanism to the tissue spreaders and operative to cause the same to transition between a neutral position, wherein the same is maintained in a coaxial configuration relative said distal end of said housing, and an extended configuration wherein the dissecting mechanism is operative to spread apart at the distal end of the housing and thus spread apart tissue to opposed sides of the distal end of the housing.

The tissue spreading dissecting mechanism transfers force from the actuator and actuator mechanism to the tissue spreaders. For example, in one such mechanism, the tissue dissecting mechanism may transmit this force to the tissue spreaders by acting as a lever or ramp at the point of contact between the tissue spreaders and the actuator cylinder. In another example, the force may be transmitted from the actuator rod through a series of pivotally connected lever arms which are themselves pivotally connected to the tissue spreaders.

Accordingly, in one embodiment, the tissue spreaders or dissector tip comprises a pair of arcuate blade members that cooperatively define a generally conical shape. The tissue spreaders are preferably operative to extend from the distal-most opening of the housing and extend in diametrically opposed directions to thus produce a spreading motion that extends beyond the opening of the distal end of the housing and thus enables a conventional viewing device to be positioned within the housing to provide the physician with direct vision as each layer of tissue is sequentially spread apart from the advancing distal end of the device. To enhance the ability of the viewing device to view past the dissector tip, the dissector tip may include arcuate voids that define apertures through which the viewing device can view into the patient when such arcuate blade members assume the general conical shape.

To the extent the distal end of the device comes within close proximity to an organ or other anatomical structure sought to be avoided, the surgeon may take appropriate measures to avoid the same. Otherwise, the physician merely advances the distal end of the device, via the sequential spreading of tissue provided by the tissue spreading dissecting mechanism, until such time as a body cavity or organ, such as the peritoneal cavity or the thoracic cavity, is entered. Once entered, a conventional endoscopic port is slid down the shaft of the housing and through the newly dissected incision into the body cavity, which advantageously can be viewed under direct vision. To enable the device to be utilized with conventional endoscopic devices and conventional endoscopic procedures, the same will preferably be made to fit various diameter ports.

Thereafter, as per conventional endoscopic procedures, the body cavity may be insufflated with carbon dioxide gas which may be channeled through the endoscopic port. In an alternative embodiment of the housing of the present invention, the housing may include a dedicated carbon dioxide channel to thus enable insulation of the body cavity to be achieved directly with the dissecting device and prior to the sliding of any endoscopic port into the body cavity.

One embodiment of the present invention provides a direct vision port site dissector that allows a surgeon to dissect a tissue under direct vision and controls penetration of the device such that inadvertent dissection of an organ, blood vessel or tissue mass can be avoided or substantially minimized.

Another embodiment of the present invention is a direct vision port site dissector that positions a port in a manner that simultaneously allows for tissue dissection coupled with port positioning and placement in a manner that substantially minimizes any possibility of leakage of carbon dioxide once the same in administered to insufflate a body cavity.

According to another embodiment, the invention consists of a port defined by a long tubular section having a proximal end and a distal end, the latter being operative to be inserted through a skin incision made upon the patient. The distal end is formed from a substantially transparent material and is operatively transitional between a first closed configuration wherein said distal end forms a closed, generally conical shape and a second expanded configuration wherein said tip is characterized by a plurality of outwardly extending tissue spreaders spreading radially outward relative the elongate tubular section. In a preferred embodiment, the distal end is biased to assume the closed configuration, and may include an additional structure such an elastic recoil or rubber covering to bias the tip to maintain the closed configuration.

Still further objects of the present invention are to provide a direct vision port site dissector or direct vision dissecting port that, in addition to substantially minimizing the risk of internal organ injury, is of simple construction, easy to use, relatively inexpensive to manufacture, and can be readily deployed utilizing conventional endoscopic surgical devices and related techniques. The device should also have a means to secure the endoscope into the device to maintain constant visual orientation and prevent the scope from slipping out of the device during dissection.

Another embodiment of the present invention includes the incorporation of electrodes into the tissue spreaders, arm members, and blade members of the dissector. The electrodes may be used for electrocautery of tissue which is being dissected.

DESCRIPTION OF THE DRAWINGS

In part, other aspects, features, benefits and advantages of the embodiments of the present invention will be apparent with regard to the following description, appended claims and accompanying drawings where:

FIG. 1 is a cross-sectional view of a direct vision dissecting port constructed in accordance with an embodiment of the present invention as utilized to gain entry into a body cavity of a patient, the dissecting port further having disposed therein an endoscope or other viewing device to enable entry into the body cavity to be viewed by a physician;

FIG. 2 is a cross-sectional view of the dissecting port of FIG. 1 wherein the distal end thereof is shown in an operative, dissecting configuration;

FIG. 13 is a cross-sectional view of an endoscopic port being positioned to gain access to a body cavity, vessel, or organ of a patient via the direct vision port site dissector of the present invention, the latter being withdrawn therefrom;

FIG. 14 is a view of the dissector tip taken along the line 14-14 of FIG. 13;

DETAILED DESCRIPTION

Figure 3:
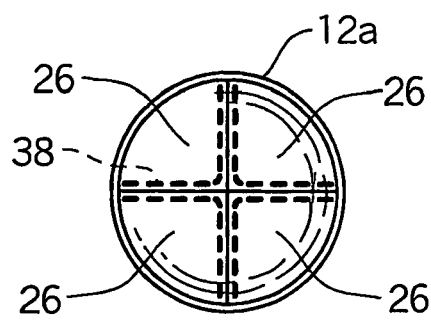
FIG. 3 is a frontal view of the distal-most tip of the dissecting port of the present invention constructed in accordance with a preferred embodiment.
Figure 4:
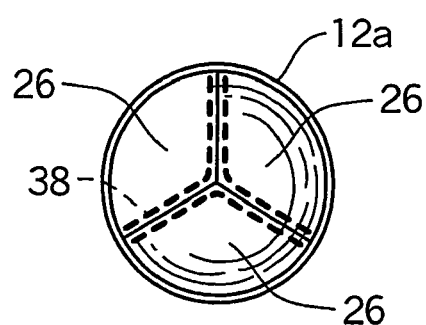
FIG. 4 is a frontal view of the distal-most tip of the dissecting port of the present invention constructed in accordance with a preferred embodiment.

The detailed description set forth below is intended as a description of the presently preferred embodiment of the invention, and is not intended to represent the only form in which the present invention may be constructed or utilized. The description sets forth the functions and sequences of steps for constructing and operating the invention. It is to be understood however, that the same or equivalent functions and sequences may be accomplished by different embodiments and that they are also intended to be encompassed within the scope of the invention.

It must also be noted that as used herein and in the appended claims, the singular forms "a", "an", and "the" include plural reference unless the context clearly dictates otherwise. Thus, for example, reference to a "cell" is a reference to one or more cells and equivalents thereof known to those skilled in the art, and so forth. Unless defined otherwise, all technical and scientific terms used herein have the same meanings as commonly understood by one of ordinary skill in the art. Although any methods and materials similar or equivalent to those described herein can be used in the practice or testing of embodiments of the present invention, the preferred methods, devices, and materials are now described. All publications mentioned herein are incorporated by reference. Nothing herein is to be construed as an admission that the invention is not entitled to antedate such disclosure by virtue of prior invention.

In the description of the present invention and embodiments thereof; the terms port and cannula may be used to describe the same device used in laparoscopic, thoracoscopic and other endoscopic surgical procedures. In these procedures the trocar or endoscope may be inserted into either the port or cannula, the trocar being used for tissue penetration and endoscopes for viewing. For purposes of this invention, the terms laparoscope, thoracoscope, mediastinascope, arthoscope and other such viewing device may be referred to using the generic term endoscope.

Referring now to the drawings, and initially to FIG. 1, there is shown a cross sectional view of a direct vision dissecting port 10 device constructed in accordance with an embodiment of the present invention. As illustrated, the dissecting port device 10 comprises an elongate housing 12 having a substantially transparent or non-opaque distal end 12a. The housing may be any shape, such as but not limited to square, rectangular, or triangular channels. Preferably the housing is tubular. The housing is operative to be inserted within an incision formed upon the skin 28 of a patient and a proximal end 12b through which a viewing device 16 and/or other surgical instruments may be deployed during a conventional endoscopic or other such surgical procedure. Substantially transparent materials, including but not limited to biologically compatible plastics, glasses, minerals and ceramics, permit viewing of the tissue at the distal end of the device. Viewing device 16 of the present invention may include but is not limited to endoscopes, laparoscopes, thoracoscopes, arthroscopes, endovascular scopes, or acoustical devices. Such viewing devices may also further comprise but are not limited to lenses and filters for magnification and viewing. Along these lines, viewing devices (e.g. as shown by viewing device 16) are well-known in the art and are typically provided with an eyepiece 16a on the proximal end thereof to enable the surgeon 18 to view surgical procedures.

According to the present invention, however, the viewing device 16 further enables the surgeon 18 to view the dissecting procedure utilized to gain access into a body cavity 36. For purposes of this invention a body cavity may include but is not limited to the peritoneal cavity, thoracic cavity, the mediastinum, the gastrointestinal tract, urinary tract, blood vessels, and structures inside the cranium. The dissecting port device 10 of the present invention not only is capable of dissecting through tissue under direct vision and serving as a conventional port, but may be used to access tissue and various organs for biopsy of such tissue or insertion of tubes for feeding or cables for other surgical devices.

With respect to the dissecting capability of the dissecting port 10 of the present invention, there is provided a handle member 14 formed upon the tubular housing or port 12 and a second handle member 22, the latter coupled with a cylindrical sleeve-like actuator 20 disposed within the lumen of the tubular housing or port 12. Handle members 14 and 22 collectively define an actuator mechanism capable of being selectively compressed and released as shown in FIG. 1 and FIG. 2.

The actuator mechanism may be located anywhere along the housing, preferably it is located along the proximal end of the housing. Alternately compressing and releasing the actuator mechanism or handle members 14, 22 transmits force through the actuator 20 to the tissue spreaders or flap members 26 and facilitates the ability of the dissecting port device 10 to selectively dissect through tissue. In an optional embodiment, a spring member 24 is disposed between handle members 14, 22 of the actuator mechanism to thus cause the handle members 14, 22 to remain in a biased state away from one another. Other actuator mechanisms may include but are not limited to screw or gear drives, magnetic, electromechanical, pneumatic or other mechanisms known to those skilled in the art. For example, it is contemplated that the cylindrical actuator 20 may take any of a variety of forms and may comprise an annular member formed on the distal end of an actuator bar or a retractable wire coupled to wire or spring mechanism 38 such that actuation of the handle members 14, 22 causes wire or spring 38 to cause tissue spreaders or flap members 26 to transition between closed and operative configurations. In a further optional embodiment, handle member 14 will have a latch 14a formed thereon and second handle member 22 will have a recess 22a formed thereon for engaging with the latch 14a to thus enable the same to remain in a locked configuration, as shown in FIG. 2. Advantageously, the ability of the handle members 14, 22 to interlock with one another facilitates the ability of the dissecting port device 10 to become anchored in position, as may be desired when the port is utilized in the performance of a surgical procedure.

The distal end 12a of the port 12, in addition to being transparent, is characterized by a plurality of tissue spreaders or flap members 26 that are operative to assume a first closed configuration, as shown in FIG. 1, whereby the tissue spreaders 26 collectively define a closed end having a generally conical shape, and a second, opened and operative configuration, shown in FIG. 2, whereby the tissue spreaders or flap members 26 radially spread out in the direction indicated by the letter "A". The number of tissue spreaders or flap members may be any number greater than two. Handle members 14, 22 facilitate the ability of the distal end 12a to selectively transition from the closed configuration depicted in FIG. 1 to the open configuration depicted in FIG. 2. In this regard, and further illustrated in FIG. 1 and FIG. 2, by compressing actuator mechanism handle members 14, 22, cylindrical actuator 20 is caused to advance distally within the tubular housing 12 such that the distal end 20a of cylindrical actuator 20 internally abuts the tissue spreaders or flap members 26 such that the same are caused to flare outwardly as shown. By retracting the actuator or actuator cylinder 20 abutting the tissue spreaders or flap members 26, the tissue spreaders 26 resume their first neutral or closed configuration. The transfer of force from the actuator cylinder 20 to the tissue spreader flap members 26 by the abutment, ramping, or leveraging action of 20 constitutes the tissue spreading dissector mechanism.

Along these lines, in any embodiment the outward expansion of the flap members 26 causes the tissue surrounding the distal end 12*a* of the port 12 to become spread apart as the distal end 12*a* of the port 12 is advanced deeper within the patient. In this regard, the distal end 12*a* will be positioned through an incision made through skin layer 28 with the tissue spreaders or flap members 26 being utilized to sequentially spread through subcutaneous fat layer 30, fascia 32, serous membrane 34 and ultimately into a body cavity 36.

Advantageously, the dissecting port device 10 of the present invention allows layers of tissue to be selectively penetrated or grasped for removal or biopsy under direct vision by the surgeon. The dissecting port device 10 may be used to biopsy tissue by withdrawal of viewing device and sampling of the tissue within the distal end of the port and closed flap members 26. The device thus enables selective entry into various tissues, body cavities, vessels, and organs to be achieved without the risk of damaging underlying or adhering tissues which can and does occur as per conventional practice. The spreading action of the device also permits selective dissection of tissue adjacent to neural and brain tissue to be made without lesions being made to the delicate neural and brain tissue.

Figure 7:
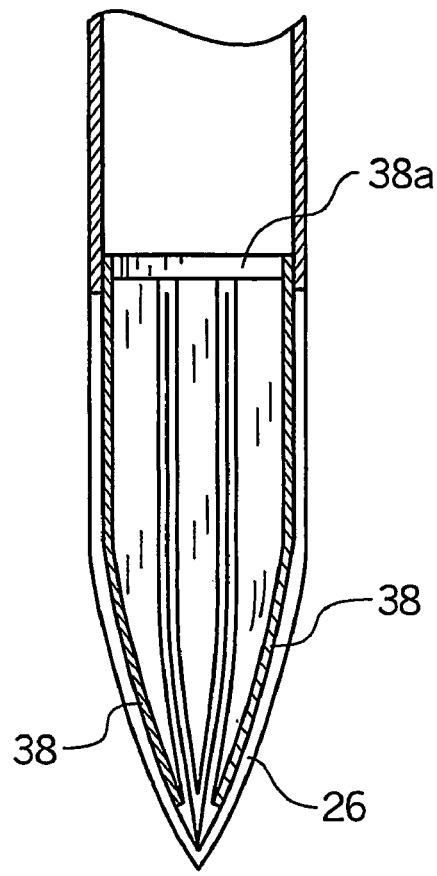
FIG. 7 is a cross-sectional view taken along the line of FIG. 6.
Figure 8:
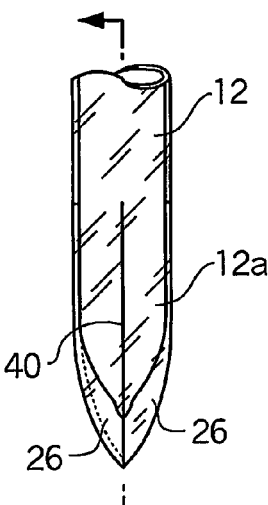
FIG. 8 is a perspective view of the distal tip of the dissecting port of the present invention constructed in accordance with another preferred embodiment, the distal tip being shown assuming a neutral, closed configuration.
Figure 9:
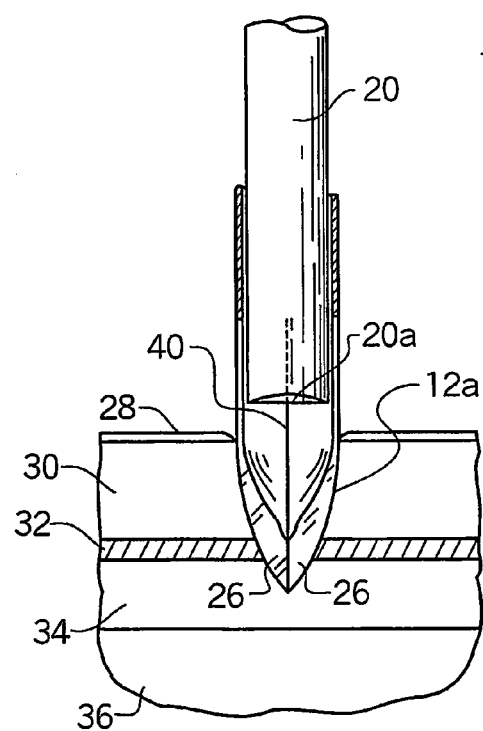
FIG. 9 is a cross-sectional view taken along the line of FIG. 8, the distal tip being utilized to gain access into the body cavity of a patient.

To better enable the tissue spreaders or flap members 26 to expand outwardly, and hence spread apart and progress through the tissue, the same may be formed to have a progressively thicker wall thickness as depicted in FIGS. 7-9. As illustrated in FIG. 7, tissue spreaders or flap members 26 have wall thickness that gradually increases toward the distal end 12*a* of the port 12. The gradually increasing wall thickness toward the distal ends of the tissue spreaders or flap members 26 enable the same to more readily spread apart as the actuator sleeve 20 is advanced. In use, an endoscope or other viewing device 16 is positioned within the port 12 and provides the physician with direct vision as each layer of tissue is sequentially spread apart by the advancing distal end of the device as illustrated in FIGS. 8 and 9. As would be known to those skilled in the art, materials useful for various components of the present invention such as the housing, actuator mechanism, and endoscope include but are not limited to biologically compatible metals such as surgical steels and titanium, as well as biologically compatible polymers, ceramics, and elastomers.

Because the tissue spreader or flap members 26 will be formed from a transparent material, the same will not hinder or otherwise obstruct the ability of the viewing device (not shown) to view the tissues laying just beyond the advancing distal end. Suitably transparent, biologically compatible, and flexible materials useful for the flaps 26 may include but are not limited to fluoropolymers such as MFA and PFA, Teflon AF from DuPont and Ausimont as well as various polycarbonates.

As depicted in FIG. 8 and FIG. 9, in use the distal end 12*a* of the housing will be inserted into and cut through the various layers of skin and soft tissue 28-34. To achieve that end, the distal end 20*a* of cylindrical actuator 20 will be sequentially advanced to the distal end, as illustrated in direction "C" of FIG. 9, to cause tissue spreading dissector mechanism flap members to spread apart along slit 40, the latter shown in FIGS. 7 and 8. As will be recognized, due to the increased wall thickness of flap members 26, there is thus provided a more rigid and durable abutment surface upon which distal end of cylindrical actuator 20*a* may contact. Moreover, such increased wall thickness will advantageously allow tissue spreading dissector mechanism flap members 26 to more forcefully and accurately dissect through the various layers of tissue 28-34.

Figure 5:
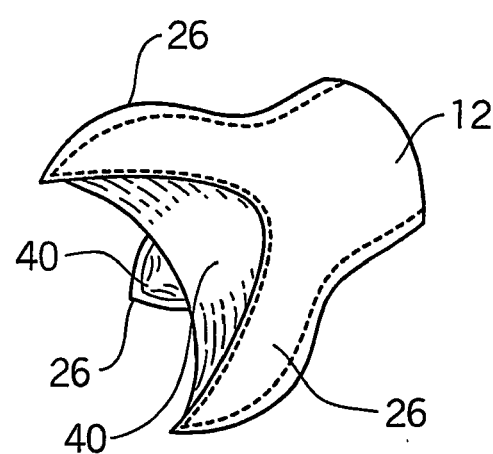
FIG. 5 is a the distal most tip of the dissecting port of the present invention at a 45° angle and in an operative, dissecting configuration.
Figure 6:
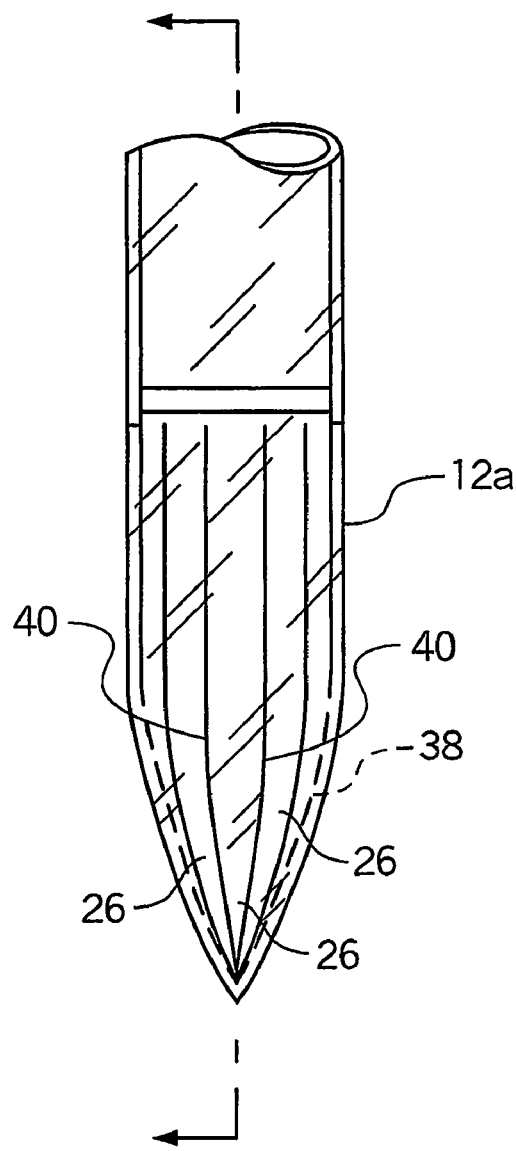
FIG. 6 is a perspective view of the distal end of the dissecting port of the present invention constructed in accordance with another preferred embodiment and assuming a neutral, closed configuration.

As will be appreciated by those skilled in the art, the tissue spreaders or flap members 26 may either be blunt or, alternatively, have a texturized or serrated outer surface (not shown) to facilitate the ability of such tissue spreading dissector mechanism flap members 26 to spread apart the tissue, or alternately grip tissue as for a biopsy. In this respect, any of a variety of texturized or sharpened objects may be formed upon the tissue spreaders or flap members 26 to facilitate the ability to cut through, grip, and spread apart tissue as the same assume the operative configurations shown in FIGS. 1 and 2 and FIGS. 8 and 9. Moreover, as shown in FIGS. 5-7, the flap members 26 may be formed to have a longer length, defined by elongate slits 40, to thus enable the flap members 26 to extend outwardly a greater distance, as may be desired in certain applications.

Along these lines, in order to better facilitate the ability of the tissue spreaders 26 of the distal end 12*a* of the tubular housing 12 to forcefully spread such layers of tissue, it is contemplated that a wire, spring, or metal reinforcement 38 may be embedded within the tissue spreaders 26 to thus provide the same with greater structural rigidity. As illustrated in FIGS. 5 and 6, such wire, spring, or metal reinforcement 38 may take any of a variety of forms, including a plurality of distally-extending leaf springs emanating from tubular section 38*a*, which are operative to bias distal end 12*a* of the housing in the closed configuration as shown.

It is also contemplated that such wire or spring reinforcement 38 may be configured such that the same bias flap member 26 to assume the closed configuration or, alternatively, lock flap members 26 in the opened configuration to thus serve as an anchoring effect. In this regard, it is contemplated that such open configuration may be maintained through the interengagement between latch 14*a* with recess 22*a* of the handle members 14, 22, as depicted in FIG. 2. By assuming such open configuration and remaining anchored into position, the dissecting port 10 of the present invention can remain securely in position throughout the surgical procedure which is ultimately performed. As will be appreciated by those skilled in the art, by remaining more securely into position, the port enables the physician to more accurately perform a surgical procedure, and/or maintain a more reliable field of view via the viewing device 16 utilized therewith. Optionally a collar may be provided around port tube 12 for positioning against skin 28 to provide additional stability of the port housing in the patient.

In accordance with an alternative embodiment of the present invention, an elastic sheath (not shown) which may alternatively take the form of an outer rubber band, rubber sleeve or the like can be used to advantageously cause the flap members 26 to assume the closed configuration shown in FIG. 1 and further present and or minimize tissue from being caught between tissue spreaders or flap members 26.

It is desirable that the distal end 12*a* of the tubular port housing 12 provide a window for the physician to directly view the dissection process as the tissue spreaders or flap members 26 selectively transition between closed and operative configurations. In this way, the physician is able to see each layer of tissue in advance of its dissection and is able to avoid puncturing or otherwise damaging organs, vessels or other structure. Of further advantage is the fact that as the dissection procedure occurs, the port 12 is also being caused to form a snug fit about the tissue as the same is cut thereby. As a consequence, the dissecting port 10 is capable of being secured within the body cavity 36 in a snug manner that can advantageously eliminate or otherwise substantially minimize any leakage of carbon dioxide gas ultimately used to insufflate the body cavity.

Along these lines, once the dissecting device port 10 is advanced into the newly dissected incision into the body cavity 36, the cavity 36 may be insufflated with carbon dioxide as per conventional endoscopic surgery. The specific endoscopic procedure may then be performed as per conventional surgical techniques. To that end it is contemplated that the dissecting port 10 will be specifically configured as per conventional ports. It is contemplated, however, that the dissecting port 10 of the present invention may be configured to be readily integrated into other types of known medical procedures or medical procedures that are later developed.

Figure 10:
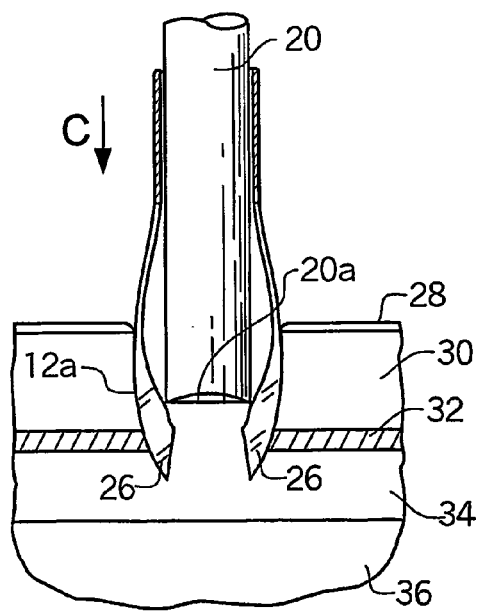
FIG. 10 is the cross-sectional view of FIG. 8 wherein the distal tip is shown assuming an operative, dissecting configuration.

Another embodiment of the present invention for spreading and proceeding through tissue under direct vision in a surgical procedure is illustrated in FIG. 10. In FIG. 10, there is shown a cross sectional view of a port site dissector 50. As illustrated, the port site dissector device 50 includes an elongate housing 52 having a distal end 52a operative to be inserted within an incision formed upon the skin 66 of a patient. The housing may be any shape, such as but not limited to square, rectangular, or triangular channels. Preferably the housing is tubular. The housing 52 has a proximal end 52b for use in coupling with a viewing device 78 and providing means for manually manipulating the dissecting device 50. With respect to the manipulating device, a first handle member 54 is preferably formed upon the distal end of the housing 52. A second handle member 56 cooperates with handle member 54 to define an actuator mechanism or handle capable of being selectively compressed in the direction indicated by the letter "A". Alternately compressing and releasing the actuator mechanism, as through movement of the handle members 54, 56, transmits force to the through actuator 60 to tissue spreading dissecting mechanism and tissue spreaders to selectively transition blade members 64 and 94 between said neutral and operative configurations enabling the port site dissector device 50 to selectively dissect through tissue. In an optional embodiment, a spring member 58 is disposed between handle members 54, 56 to thus cause the handle members 54, 56 to remain in a biased state away from one another.

Figure 15:
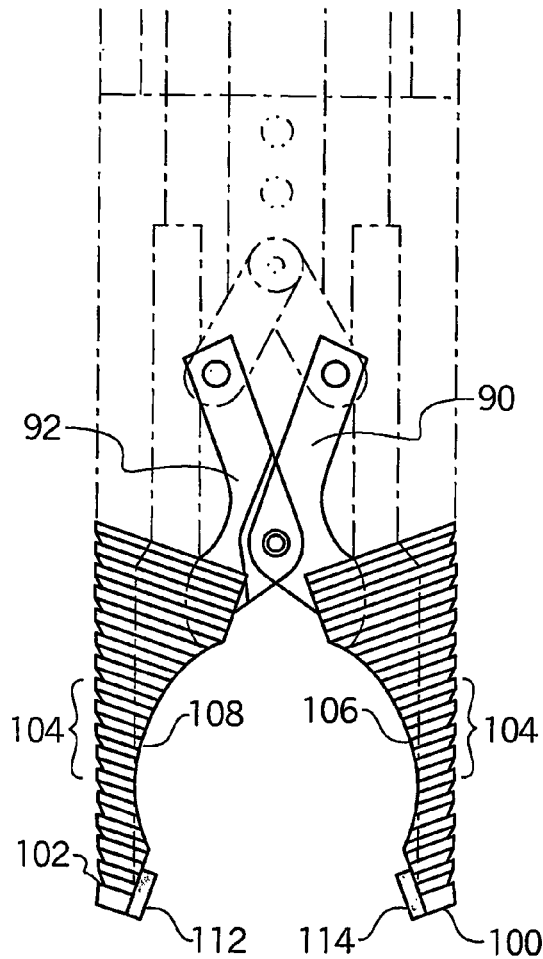
FIG. 15 is a side-view of a dissector tip of the direct vision port site dissector of the present invention, constructed in accordance with a preferred embodiment, shown in a second operative position.
Figure 16:
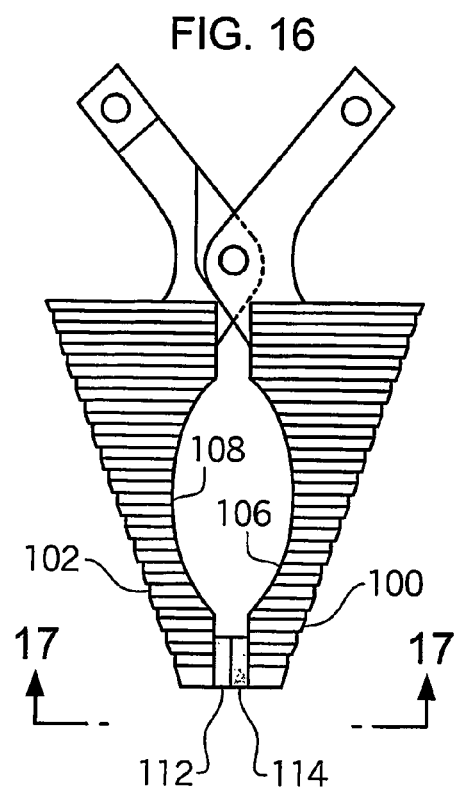
FIG. 16 is a side view of the dissector tip of FIG. 15 shown in a first neutral position.
Figure 17:
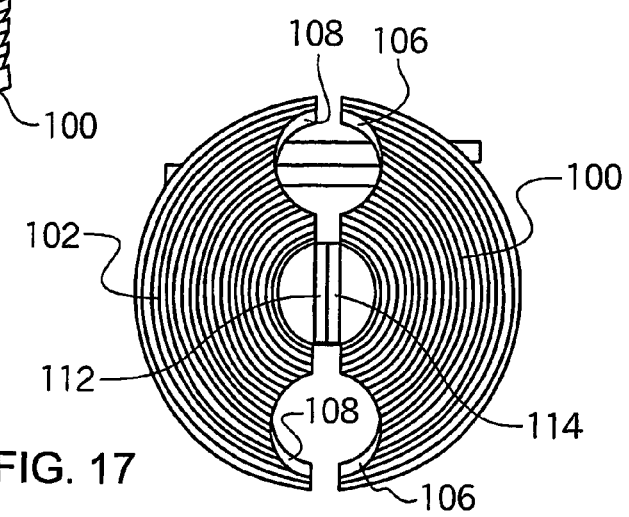
FIG. 17 is a frontal view taken along line 17-17 of FIG. 16.

Actuator mechanisms may include but are not limited to springs, screw or gear drive, magnetic, electromechanical, pneumatic or other mechanisms known to those skilled in the art. The actuator mechanism may be positioned anywhere along the housing 52, preferably it is formed near the proximal end of the housing. The actuator mechanism force may be transmitted to the actuator 60 and then to the tissue spreading dissector mechanism in various ways. The actuator 60 may be but is not limited to rods, shafts, cylinders, or threaded rods. Attached to, or preferably integrally formed with the actuator mechanism or handle 56 is actuator bar 60, the latter extending in general parallel relation to tubular housing 52 and terminating near distal end 52a thereof. Attached to the distal-most end of actuator bar 60 is a tissue spreading dissector mechanism 62 operative to selectively spread tissue, via a dissector tip, the latter preferably comprising diagonally extending arm members 86, 88 pivotally connected to the distal end of actuator bar 60 and an opposed pair of tissue spreaders 64, 94, more clearly seen in FIGS. 11 and 14, to thus enable layers of tissue to be selectively spread apart as the port site dissector device 50 is advanced through the various layers of tissue, for example, subcutaneous fat layer 68, fascia 70, serous membrane 72 and ultimately into the body cavity 74. Another opposed pair of tissue spreaders 100, 102, which reflect another embodiment of the present invention, are depicted in FIGS. 14-16.

Advantageously, the port site dissector device 50 of the present invention enables such layers of tissue to be selectively penetrated or grasped for removal or biopsy under direct vision by the surgeon. The device thus enables selective entry into various tissues, body cavities, vessels, and organs to be achieved without the risk of damaging underlying or adhering tissues which can and does occur as per conventional practice. The spreading action of the device also permits selective dissection of tissue adjacent to neural and brain tissue to be made without lesions being made to the delicate neural and brain tissue.

To achieve that end, the device 50 is operative to receive a viewing device 78 within the tubular housing 52 thereof to thus provide a physician with the ability to directly view the sequential dissection of the various layers of tissue via the dissector 50 of the present invention. As shown in FIG. 10, viewing device 78 is operatively positioned within the tubular housing 52 such that the distal-most end of the viewing device 78a is positioned in close proximity to the tissue spreading dissector mechanism 62 with spreader members 64, 94 to thus enable the physician to view each step of the dissection process. To facilitate the ability of the device 50 to receive the viewing device 78, there may be provided a clamp mechanism 82 formed upon proximal end 52b of the housing 52, with screw lock 84 to thus enable the same to be locked into position. The clamp mechanism may also be engaged to securely hold the viewing device 78 into position within the lumen of the housing or may be disengaged to allow free rotation of the scope within the lumen of the housing. The locking mechanism may also be released for removal of the viewing device from the housing lumen to change endoscopes or to perform cleaning on them. There may additionally be provided an abutment apparatus or other type of engagement mechanism 52c formed with the lumen of housing 52 to prevent the distal end 78a of the viewing device from extending beyond distal end 52a of the housing. Once secured into position, the eyepiece provided on the proximal end 78b of the viewing device, as per conventional endoscopes, enables the surgeon to see and directly view the dissection procedure.

Figures 11, 12:
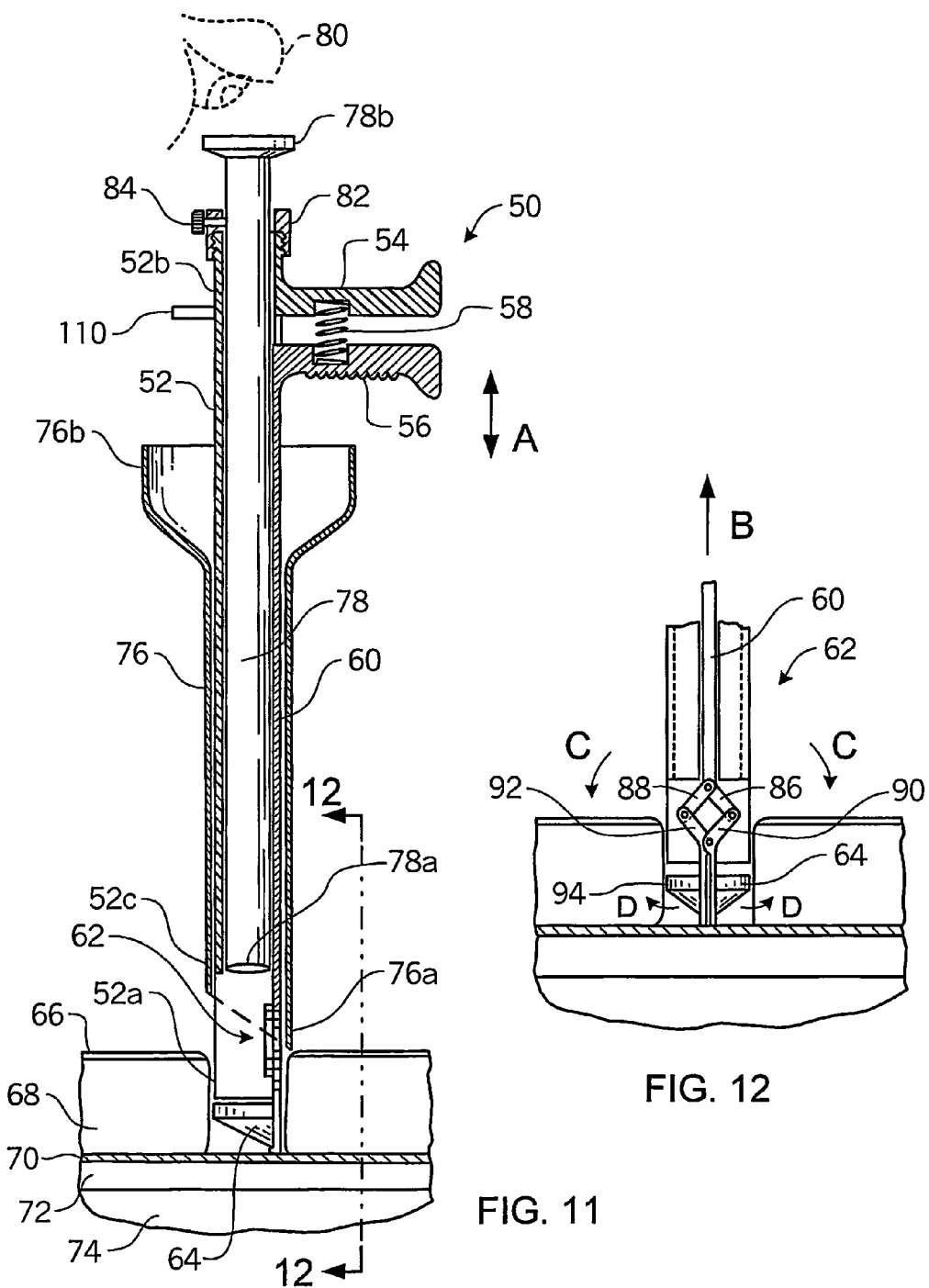
FIG. 11 is a cross-sectional view of a direct vision port site dissector constructed in accordance with the preferred embodiment of the present invention as utilized to gain entry into a body cavity, vessel, or organ of a patient, the port dissector further having included therein an endoscope, or other viewing device to enable entry into the body cavity to be viewed by a physician.
FIG. 12 is a perspective view taken along line 12-12 of FIG. 11.

As further shown in FIG. 10, the device 50 is operative to be axially received within the lumen of a conventional endoscopic port 76 such that once access into the body cavity has been safely achieved, the port 76 may be secured into position so that the subsequent surgical procedure may be performed. Referring now to FIGS. 11 and 13, and with initial reference to FIG. 11, there is shown the means by which tissue spreading dissector mechanism 62 is operative to cause the dissector tip, namely, tissue spreader members 64 and 94, to selectively dissect through the various layers of tissue to gain access to the body cavity, organ, or vessel. As is shown, when actuator bar 60 is retracted in the direction indicated by the letter "B", which occurs through compression of actuator mechanism or handle members 54, 56, diagonally extending arm members 86, 88 pivotally connected to the distal end of actuator bar 60 are operative to rotate inwardly as indicated by the direction "C". A second pair of arm members 90, 92, pivotally connected to arms 86, 88, respectively, are then consequently operative to rotate outwardly from the distal—most end 52a of tubular housing 52, as indicated by the direction "D", to thus cause tissue spreader members 64, 94 to spread apart, separate, cut through, and move tissue away therefrom. In this regard, the tissue spreaders 64, 94, will be operatively transitionable between a first neutral configuration or position, as shown in FIG. 13, whereby the same are contained within the diameter defined by the distal end 52a of the tubular housing 52 and an operative configuration, whereby the tissue spreader members 64, 94, may extend to or beyond the circumference defined by the distal end 52a of the tubular housing 52 to thus spread apart the tissue as the distal end 52a of the tubular housing 52 is advanced deeper within the patient.

In use, the device 50 is utilized to sequentially spread layers of tissue 68, 70, and 72 until such time as the body cavity, vessel, or organ is accessed or a tissue for a biopsy is removed. As illustrated in FIG. 12, the device 50 is shown with endoscopic port 76 just entering the serous membrane. To achieve that end, tissue spreaders 64, 94, will preferably comprise arcuate blade members that cooperatively define a generally conical-like structure when the same assume the neutral position, as shown in FIGS. 11 and 13. When the spreader members 64, 94 assume the operative configuration, the same will extend in diametrically opposed directions to thus cause the tissue to be dissected in an outwardly-extending direction relative to the distal end 52a of the housing 52. Tissues spreaders, for example but not limited to those like 64 and 94, are advantageous for penetrating delicate brain tissues or body cavity walls with adherent organs because their edges may be suitably shaped to slowly penetrate the tissue and minimize cutting or lesioning of underlying tissue and organs.

Such mode of tissue penetration action is further illustrated, for example, in FIGS. 14-16 with respect to alternatively configured tissue spreaders 100, 102, of the dissector tip. As shown in FIG. 14, the tissue spreaders 100, 102, are shown in the operative position whereby the same extend in diametrically opposed directions from the distal end of the tubular housing 52. Tissue spreaders, for example but not limited to those like 100, 102, and in contrast to the embodiment depicted in FIGS. 10-13, are provided with serrated edges 104, as may be desired to facilitate the ability of the tissue spreader 100, 102, to advance through tissue.

The tissue spreaders 100, 102, may further be provided with arcuate voids 106, 108, that cooperate to define generally circular or oval-shaped apertures when the tissue spreaders 100, 102, assume the neutral position, as shown in FIG. 15. Advantageously, by providing arcuate voids 106, 108, which define such apertures, there is thus provided channels or access by which a viewing device 78 (not shown) can directly view the tissue directly ahead of the dissector tip while the tissue spreaders 100, 102 assume a neutral position as shown in FIGS. 15 and 16.

It will be appreciated by those skilled in the art that although depicted as semi-circular blade members, tissue spreaders 64, 94, 100, 102 may take any of a variety of configurations known in the art, and may include any of a variety of tissue spreading mechanisms including additional tissue spreader members. A number of shapes, sizes, or configurations of the dissecting tip may be used in the present invention without limitation as would be obvious to one skilled in the art. The shape, size or configurations of such tissue spreaders or dissecting tips will be chosen based upon its suitability for particular operation or procedure with consideration given to but not limited to tissue type and depth to be removed, underlying tissue or organ, required port size. In all cases, however, it is desired that the tissue spreaders be operative to sequentially spread layers of tissue out of the field of vision to be observed by the distal end 78a of the endoscope or other viewing or recording device 78 to thus enable the physician at all times to see the tissue, during both when the tissue spreader members assume either the neutral or operative configurations until such time as the endoscopic or other such port 76 is advanced into the channel formed by the dissection of tissue by the tissue spreaders and the device 50 removed therefrom, as shown schematically in FIG. 12.

As would be known to those skilled in the art, materials useful for various components of this embodiment of the present invention such as the housing, actuator mechanism, tissue spreaders, arm members, and endoscope include but are not limited to biologically compatible metals such as surgical steels and titanium, as well as biologically compatible polymers, ceramics, and elastomers.

At all steps during the procedure the distal end 78a of endoscope, or other viewing device 78 is operative to provide the physician with a direct view of the dissection process as the tissue spreader members 64, 94, or 100, 102 selectively transition between their neutral position, and the operative tissue spreading configuration. As such, at all times, the physician is able to see each layer of tissue in advance of its dissection and is able to avoid puncturing or otherwise damaging an organ, vessel or other structure. Of further advantage is the fact that the dissector 50 of the present invention is operative to spread apart tissue as the distal end 52a of the housing 52 is advanced axially downward. As a consequence, a snug fit is formed about the tubular housing 52, which in turn provides for a snug fit about the port 76 once the same is ultimately secured into position, as shown in FIG. 12.

As will be recognized by those skilled in the art, the dissector 50 may be used to biopsy a tissue and enables the physician to avoid injuring adjacent organs, vessels, nerves, and the like. The dissector may also enable the port 76 to be secured into position with the body cavity in a snug manner to advantageously eliminate or otherwise substantially minimize any leakage of carbon dioxide gas ultimately used to insufflate a body cavity or to seal about tubes or other feedthroughs for use by a surgeon. In this respect, not only will entry into the body cavity be entered in a manner that avoids any risk to organs, vessels, and the like, it likewise enables a port to be placed into position without the need to provide any sort of prior insufflation.

Once the port 76 is advanced into the newly dissected incision into the body cavity, for example the peritoneal or thoracic, the body cavity may be insufflated with carbon dioxide as per conventional surgery. The specific endoscopic procedure may then be performed as per conventional surgical techniques. Along these lines, it is contemplated that the device 50, and more particularly the tubular housing 52, thereof, will be specifically configured to fit conventional ports. It is contemplated, however, that the same may be sized and adapted to fit any of a variety of conventional endoscopic port sizes and or adapted to receive and be utilized with any of a variety of endoscopes or other viewing devices to thus enable the same to be readily integrated into conventional medical procedures.

Embodiments of the device of the present invention are designed for the safe entry into various body cavities under direct visual dissection of the tissues in order to prevent inadvertent organ injury. For example, the device may be used for entry into the previously operated abdomen with the likelihood of intra-abdominal adhesion being fairly high, as such, it may be useful as a replacement for the Hasson technique. As the majority of significant adhesions are to the area under the previous incision, the device can be used either to enter the abdominal cavity in the midline above or below the previous incision where organ or tissue adhesion is less likely. The device can also be used to enter the abdominal cavity in other areas such as the lateral abdominal wall where tissue or organ adhesion is less likely. In this case the device has distinct advantages over the Hasson technique as the Hasson technique is cumbersome to perform when entering through the three separate layers of the lateral abdominal wall, requiring a larger incision and longer operative time, while embodiments of the device of the present invention were designed for such entry and can be used to enter laterally via an incision no larger than that necessary to admit the endoscopic port. The device is also ideally suited for entry into the unoperated abdomen as well, avoiding the necessity of three blind phases of laparoscopic or endoscopic surgery: Veress needle insertion, insufflation, and blind trocar insertion.

The present invention may also be used to enter the thoracic cavity through the pleural membrane while minimizing the risk of damage to adjacent lung tissue. As an increasing number of thorascopic procedures are now being performed under condition of controlled pneumoperitoneum, the dissection provided by the present invention will provide a tight seal with the port ensuring minimal gas leakage which is desirable to the completion of the procedure.

The present invention may also be used to dissect, under direct vision, and with significant magnification, vital structures, during the course of surgery after the insufflation has been established.

Embodiments of the present invention are well suited to robotic or virtual reality surgery as the device can rely on visual cues, rather than tactile sensation required for entry using other optical trocars, some of which require a great deal of force to be applied in order to enter a body cavity such as the abdominal cavity. Typically it is the surgeon's judgment that determines when the trocar will enter the abdominal cavity. Optical methods may be used to distinguish tissue types being dissected by the device and may be used in a closed loop servo system with the tissue spreaders of the present invention to control the rate of penetration of the device through tissues in a patient. Additionally, since the resistance of the tissue in many dissections decreases rapidly upon entry into a body cavity, force sensors may also be used with the tissue spreaders of the present invention to monitor, through a controller, and ensure that the device does not over-penetrate on entry to the cavity risking significant organ injury.

Embodiments of the present invention may be used safely to dissect under direct magnified vision, any body cavity or potential space such as the peritoneal cavity, thoracic cavity, pre-peritoneal space, retro-peritoneal space or intraluminal space. Embodiments of the present invention may be particularly advantageous in neurosurgery or other surgeries involving the nervous system, where small incisions in the skin overlying the skull or spine can be made and the dissection to or dissection of the structures of interest inside the cranium or near the spine can be approached under direct vision without the use of sharp downward cutting edges.

Modern endoscopic procedures often control a patient's bleeding in the surgical site through the use of electrocautery. As used herein, the phrases cautery, electrocautery, and coagulation may be used interchangeably.

Monopolar cauterization is a method of cauterizing tissue with a single electrified metal tip. The electricity is concentrated at the tip of the instrument where is conducts from the instrument to the patient and causes sealing blood of vessels as current flows to a larger grounding pad. One skilled in the art would understand how one or both of the mobile tips of the port site dissector could be electrified to provide both monopolar cautery or bipolar cautery.

Bipolar electrocautery instruments generally include two electrodes closely spaced for contact with organs and tissue of the patient. The electrodes are electrically isolated from each other and include a separate current path back through to a current connector located adjacent the handle of the instrument. The current connectors are in electrical communication with a suitable power supply. Thus, during contact of the bipolar instrument with an organ or tissue of the patient, electric current flows from the first electrode through the tissue which is then cauterized, and then to the second electrode of the bipolar instrument.

Embodiments of the present invention may also include electrodes for electrocautery. The flaps, blade member, or arm member tips of the dissector may be or have incorporated into them an electrocautery element. The tips may be made either monopolar or bipolar by connection to a source of electric current such that the tip of the dissector may be used to selectively cauterize blood vessels or tissue encountered in the dissection. For example, as shown in FIG. 10, the electrocautery element in the tips can be connected via a thin insulated wire (not shown) running within or inside the tube structure towards the proximal end, to an electrical connector 110 extending outward from the body of the device which would be connectable to a standard electrocautery power source. In FIG. 10 the proximal end of the housing 52*b* may be provided with a wire which may have one or more insulated conductors from connector 110 within the housing 52 which electrically connects one or both of the blade members 64 and 94 to the power supply (not shown). The housing 52 may include a switch (not shown) to selectively permit the operator of the dissector to allow or stop the flow of current to the electrodes. In FIG. 13 one or both of the arm members 90 or 92 may be electrically energized to act as tips or electrodes for electro-cautery. Where the blade members or arm members function as an electrode they should be made of a chemically compatible and electrically conductive material. Electrically insulating gaskets may be used to isolate arm members at their pivot points or insulating gripping members 112 and 114 may be used to provide for bipolar operation of the arm members or the blade members as electrodes. A filament or electrode may be applied to the surface or recessed into flap members 26, arm members, or blade members and connected to a source of electric current for monopolar or bipolar electrocautery.

Embodiments of the present invention may also be used for grasping and sampling tissue since the tissue spreader jaws can be actuated forcibly into both open and closed positions. As such, the device may used to penetrate a tissue and selectively biopsy portions of it, for example removal of a polyp or cyst, during the dissection for later examination in order to establish a precise diagnosis. This application could be used potentially in flexible endoscopy such as but not limited to colonoscopy, upper endoscopy, and urethroscopy and ureteroscopy. An embodiment of the present invention with suitably shaped tissue spreaders may be configured in a flexible endovascular scope, and as such may be used for the direct angioplasty of vessels as well as other endovascular surgeries.

Additional modifications and improvements of the present invention may also be apparent to those of ordinary skill in the art. For example, it is contemplated that the port dissector device 10 or device 50 may include a separate port to enable the body cavity to be insufflated with carbon dioxide, rather than requiring that the port site dissector device 10 or 50 be withdrawn from the body and the carbon dioxide administered separately. In another example, actuator bar 60 may be configured such that separation of handle members 54, 56 causes such bar 60, via tissue spreading dissector mechanism 62 attached thereto, to selectively dissect through tissue. In yet another example, device 10 and port 12 may be used to initially access a body cavity and maintain insufflation with flaps 26 closed. Thereafter viewing device 16 may be removed and replaced with tubular housing 52, tissue dissecting mechanism 62 and blades 100 and 102 for selective biopsy of a tissue within the body cavity under direct vision by viewing device 16. Thus, the particular combination of parts and steps described and illustrated herein is intended to represent only certain embodiments of the present invention, and is not intended to serve as limitations of alternative devices and methods within the spirit and scope of the invention.

What is claimed:

1. A dissector device useful for dissecting a tissue comprising:
    an elongated housing comprising an elongated tubular section and having proximal and distal ends and a lumen, said distal end being operative to be inserted within a surgical incision, said housing further comprising a viewing device positioned within the lumen, wherein the viewing device is oriented to view through the distal end of said housing;
    a tissue spreading dissector mechanism formed upon said distal end of said housing, said tissue spreading dissector mechanism operatively transitional between: a first neutral configuration wherein said tissue spreading dissector mechanism extends from the distal end of said housing; and an operative configuration wherein said tissue spreading dissector mechanism extends outwardly beyond a circumference defined by said elongated tubular section, and said tissue spreader dissecting mechanism comprising opposed blade members configured to provide at least one void formed thereon defining a channel through which said viewing device can view through the distal end of said housing; and
    an actuator mechanism formed upon said proximal end of said housing operative to selectively cause said tissue spreading dissecting mechanism and tissue spreaders to selectively transition between said neutral and operative configurations.

2. The dissector of claim 1 wherein the opposed blade members are operative to extend in diametrically opposed directions from said distal end of said housing when said tissue spreader dissecting mechanism assumes operative configurations.

3. The dissector of claim 2 wherein said dissector further includes a clamp mechanism for securably holding said viewing device into position within said lumen of said housing.

4. The dissector of claim 3 wherein said clamp mechanism is formed upon said proximal end of said housing.

5. The dissector of claim 1 wherein said housing further includes a stop member formed within the lumen thereof for limiting the distance said viewing device or endoscope can extend distally within said tubular housing.

6. The dissector of claim 1 wherein said actuator mechanism is an actuator bar operatively coupled to handle members and said tissue spreading dissector mechanism, said actuator bar being operative to cause said tissue spreading dissector mechanism to selectively transition between said neutral and operative configurations when said handle members are actuated.

7. The dissector of claim 1 wherein said tissue spreading dissector mechanism comprises a first pair of arms pivotally mounted to an actuator rod and a second pair of arms coupled to said first pair of arms and operative to pivot outwardly relative to said first pair of arms, said second pair of arms having tissue spreader members formed on the respective ends thereof that are operative to transition from said neutral and operative configurations as said first and second arm members pivotally move relative to one another.

8. The dissector of claim 1 wherein said dissector further comprises a channel formed therein for administering an insufflative gas.

9. The dissector of claim 1 wherein said dissector is capable of being axially received within a port.

10. The dissector of claim 9 wherein said dissector is insertable through a port or cannula.

11. The dissector of claim 2 wherein said opposed tissue spreader blade members cooperate to define a conical-shaped configuration when assuming said first neutral position.

12. The dissector of claim 1 wherein the tissue spreaders of the tissue dissecting mechanism are in electrical communication with a source of electric current, said tissue spreader used for selectively cauterizing tissue.

13. The dissector of claim 1 wherein said tissue spreading dissector mechanisms comprises a plurality of tissue spreaders having one or more serrated outer edges positioned to facilitate advancement of the tissue spreader through the tissue.

* * * * *